United States Patent [19]

Henco et al.

[11] Patent Number: 5,677,147

[45] Date of Patent: *Oct. 14, 1997

[54] HIV-2 VIRUS VARIANTS

[75] Inventors: Karsten Henco, Erkrath; Hagen von Briesen, Kronberg; Andreas Immelmann, Dusseldorf; Herbert Kühnel, Egelsbach; Ursula Dietrich, Eschborn; Helga Rübsamen-Waigmann, Bad Soden am Taunus; Michalina Adamski, Frankfurt, all of Germany

[73] Assignees: Qiagen GmbH, Hilden; Chemotherapeutisches Forschunginstitut Georg-Speyer-Haus, Frankfurt am Main, both of Germany

[*] Notice: The portion of the term of this patent subsequent to Dec. 14, 2014, has been disclaimed.

[21] Appl. No.: 684,682

[22] Filed: Jul. 22, 1996

Related U.S. Application Data

[63] Continuation of Ser. No. 358,575, Dec. 14, 1994, Pat. No. 5,637,455, which is a continuation of Ser. No. 994,081, Dec. 16, 1992, abandoned, which is a continuation of Ser. No. 365,568, Jun. 14, 1989, abandoned.

[30] Foreign Application Priority Data

Jun. 14, 1988 [DE] Germany ............... 38 20 223.9

[51] Int. Cl.$^6$ .................................................. C12N 5/10
[52] U.S. Cl. .................. 435/69.3; 435/325; 435/239; 435/366; 435/367; 435/372; 435/372.3; 435/974; 435/235.1; 532/826
[58] Field of Search ........................... 435/235.1, 239, 435/240.1, 240.2, 974, 325, 366, 367, 372, 372.1–372.3, 69.3; 530/826

[56] References Cited

U.S. PATENT DOCUMENTS 4,956,292  9/1990  Chermann et al. ............... 435/5

FOREIGN PATENT DOCUMENTS

| 0269520 | 6/1988 | European Pat. Off. . |
| 0327801 | 8/1989 | European Pat. Off. . |
| WO8909815 | 10/1989 | WIPO . |

OTHER PUBLICATIONS

Gartner et al, Science 233:215–219 (1986).
Koenig et al, Science 233:1089–93 (1986).
Koyanagi et al. Science 236:819–822 (1987).
Saunders Dictionary & Encyclopedia Laboratory Medicine & Technology 1974 pp. 211–217.
Wiley et al, Proc Natl Acad Sci USA, 83:7089–93 (1986).
Cheng–Mayer et al, Proc Natl Acad Sci USA, 84: 3826–30 (1987).
Jan Albert et al., "A New Human Retrovirus Isolate of West African Origin (SBL–6669) and Its Relationship to HTLV–IV, LAV–II, and HTLV–IIIB"; vol. 3, No. 1, 1987, AIDS Research and Human Retroviruses, Mary Ann Liebert, Inc., publishers.
S.K. Arya et al., "New human and simian HIV–related retroviruses process functional transactivator (tat) gene" Nature, vol. 328, Aug. 6, 1987, pp. 548–550.
H. Kuhnel et al., "Molecular cloning of two West African human immunodeficiency virus type 2 isolates that replicate well inmacrophages"... Proc. Natl. Acad. Sci. USA, vol. 86, Apr. 1989, pp. 2383–2387.
Mireille Guyader et al., "Genomeorganization and transactivation of the human immunodeficiency virus type 2" Nature, vol. 326, Apr. 1987, pp. 662–669.
Beatrice H. Hahn, et al., "Molecular cloning and characterization of the HTLV–III virus associates with AIDS" Nature, vol. 312, Nov. 8, 1984, pp. 166–169.
H. Rubsamen–Waigmann et al., Isolation of variants of Lymphocytopathic Retroviruses From the Peripheral Blood and Cerebrospinal Fluid of Patients with ARC or AIDS, Journal of Medical Virology 19:335–344 (1986).
H. von Briesen et al., Isolation Frequency and Growth Properties of HIV–Variants: Multiple Simultaneous Variants in a Patient Demonstrated by Molecular Cloning, Journal of Medical Virology 23:51–66 (1987).
A.B. Rabson et al., "Molecular Organization of the AIDS Retrovirus" vol. 40, pp. 477–480 Mar. 1985.

*Primary Examiner*—Christine M. Nucker
*Assistant Examiner*—Jeffrey Stucker
*Attorney, Agent, or Firm*—Jacobson, Price, Holman & Stern, PLLC

[57] ABSTRACT

HIV-2 virus variants, namely virus HIV D194 and virus HIV D205, which can be cloned from the corresponding virus isolate HIV D194 (ECACC V 87122303) or from the infected cell line HUT 194 (ECACC V 87122306) or from the virus isolate HIV D205 (ECACC V 87122304), respectively, and their RNA or RNA-fragments and DNA and DNA-fragments derived therefrom and/or proteins and the use thereof for diagnostics and therapy.

4 Claims, 24 Drawing Sheets

FIG. 1

|      | Nucleotide Sequence | Amino Acid Sequence |
|------|---------------------|---------------------|
| gp41 | about 15%           | about 21%           |
| p24  | about 13%           | about 8%            |

D    V    W    H    L    F    E    T    S    I    K    P    C
HIV2  ROD   GAT  GTC  TGG  CAT  CTA  TTC  GAG  ACA  TCA  ATA  AAA  CCA  TGT
HIV2  D194  ···  ···  ···  AGA  ···  ..T  ···  ···  ···  ···  ···  ···  ···
             D    V    W    R    L    F    E    T    S    I    K    P    C

V    K    L    T    P    L    C    V    A    M    K    C    S
HIV2  ROD   GTC  AAA  CTA  ACA  CCT  TTA  TGT  GTA  GCA  ATG  AAA  TGC  AGC
HIV2  D194  ···  ..G  T.G  ..G  ..C  C..  ···  ..G  ..G  ···  ..T  ...T --
             V    K    L    T    P    L    C    V    A    M    K    C    -

S    T    E    S    S    T    G    N    N    T    T    S    K
HIV2  ROD   xxx  xxx  xxx  xxx  xxx  xxx  xxx  xxx  xxx  xxx  xxx  xxx  xxx
HIV2  D194  --   --   --   --   --   --   --   --  ..T  .T.  ..T  ···  --
             -    -    -    -    -    -    -    -    N    I    T    S    -

S    T    S    T    T    T    T    T    P    T    D    Q    E
HIV2  ROD   AGC  ACA  AGC  ACA  ACC  ACA  ACC  ACA  CCC  ACA  GAC  CAG  GAG
HIV2  D194  --   --  G.G  ..T  ···  G.G  ···  C.G  AGT  C..  CCA  A.C  ATT
             -    -    G    T    T    A    T    P    S    P    P    N    I

Q    E    I    S    E    D    T    P    C    A    R    A    D
HIV2  ROD   CAA  GAG  ATA  AGT  GAG  GAT  ACT  CCA  TGC  GCA  CGC  GCA  GAC
HIV2  D194  AC.  ATA  ···  GA.  ..A  A..  T..  A.C  ..T  AT.  G..  .AC  .GC
             T    I    I    D    E    N    S    T    C    I    G    D    G
```

FIG. 4

```
         10         20         30         40         50         60
  AGTCGCTCTG CGGAGAGGCT GGCAGATTGA GCCCTGGGAG GTTCTCTCCA GCACTAGCAG
         70         80         90        100        110        120
  GTAGAGCCTG GGTGTTCCCT GCTAGACTCT CACCAGTGCT TGGCCGGCAC TGGGCAGACG
        130        140        150        160        170        180
  GCTCCACGCT TGCTTGCTTA AAGACCTCTT AATAAAGCTG CCAGTTAGAA GCAAGTTAAG
        190        200        210        220        230        240
  TGTGTGTTCC CATCTCTCCT AGTCGCCGCC TGGTCATTCG GTGTTCATCT GAGTAACAAG
        250        260        270        280        290        300
  ACCCTGGTCT GTTAGGACCC TTCCCGCTTT GAGAATCCAA GGCAGGAAAA TCCCTAGCAG
        310        320        330        340        350        360
  GTTGGCGCCC GAACAGGGAC TTGAAAGAGG ACTGAGAAGC CCTGGAACAC GGCTGAGTGA
        370        380        390        400        410        420
  AGGCAGTAAG GGCGGCAGGA ACAAACCACG ACGGAGTGCT CCTAGAAAAG CGCGGGCCGA
        430        440        450        460        470        480
  GGTACCGAAG CGGCGTGTGG AGCGGGAGTG AAAGAGGCCT CCGGGTGAAG GTAAGTACCT
        490        500        510        520        530        540
  ACACCGAAAA CTGTAGCCAG AAAAGGCTTG TTATCCTACC TTTAGACAGG TAGAAGATTG
        550        560        570        580        590        600
  TGGGAGATGG GCGCAGAAAA CTCCGTCTTG AGAGGGAAAA AAGCAGACGA ATTAGAAAAA
        610        620        630        640        650        660
  GTTAGGTTAC GGCCCAACGG AAAGAAAAGA TACAGGTTAA AACATGTTGT GTGGGCAGCG
        670        680        690        700        710        720
  AATGAATTAG ACAGATTCGG ATTGGCAGAG AGCCTGTTGG AATCAAAAGA AGGTTGCCAA
        730        740        750        760        770        780
  AAGATTCTTA AAGTTTTAGA ACCATTAGTA CCAACAGGGT CAGAAAATTT AAAAAGCCTT
        790        800        810        820        830        840
  TTTAATACCG TCTGCGTCAT TTGGTGCTTG CACGCAGAAG AGAAAGTGAA AGATACTGAA
        850        860        870        880        890        900
  GAAGCAAAGA AACTAGCACA GAGACATCTA GTGGCAGAAA CAGGAACTGC AGAGAAAATG
        910        920        930        940        950        960
  CCAAATATAA GTAGACCAAC AGCACCACCT AGTGGGAAAG GGAGGAAACT TCCCCGTGCA
        970        980        990       1000       1010       1020
  ACAGGCAGGC GGCAACTATA TCCATGTGCC GCTGAGCCCC CGAACTCTAA ATGCTTGGGT
       1030       1040       1050       1060       1070       1080
  AAAATTAGTA GAGGAAAAGA AGTTCGGGGC AGAAGTAGTG CCAGGATTTC AGGCACTCTC
       1090       1100       1110       1120       1130       1140
  AGAAGGCTGC ACGCCCTATG ATATCAATCA AATGCTTAAT TGTGTGGGCG ATCACCAAGC
```

FIG. 4A

```
      1150        1160       1170       1180       1190       1200
 AGCTATGCAA  ATAATCAGAG  AAATTATTAA  TGAGGAAGCA  GCAGATTGGG  ATGCGCAGCA
      1210        1220       1230       1240       1250       1260
 CCCAATACCA  GGCCCCTTAC  CAGCAGGGCA  GCTTAGAGAC  CCAAGGGGGT  CTGACATAGC
      1270        1280       1290       1300       1310       1320
 AGGAACAACA  AGCACAGTAG  ATGAACAGAT  CCAGTGGATG  TATAGGCAAC  CAAATCCCGT
      1330        1340       1350       1360       1370       1380
 GCCGGTAGGG  AACATCTACA  GGAGATGGAT  CCAGATAGGG  CTACAGAAAT  GTGTCAGGAT
      1390        1400       1410       1420       1430       1440
 GTACAACCCA  ACTAACATCT  TAGATGTGAA  GCAGGGACCA  AAAGAATCGT  TCCAGAGCTA
      1450        1460       1470       1480       1490       1500
 TGTAGACAGA  TTCTACAAAA  GCCTAAGGGC  AGAACAAACA  GACCCGGCTG  TAAAAAATTG
      1510        1520       1530       1540       1550       1560
 GATGACCCAA  ACGCTGCTAA  TACAGAATGC  CAACCCAGAC  TGCAAGTTAG  TATTAAAAGG
      1570        1580       1590       1600       1610       1620
 ACTAGGGATG  AATCCCACCC  TAGAGGAGAT  GCTGACTGCC  TGCCAGGGAG  TAGGCGGACC
      1630        1640       1650       1660       1670       1680
 AAGCCAGAAA  GCCAGACTAA  TGGCTGAAGC  CCTAAAGGAG  GCTTTGACGC  CAGCCCTAT
      1690        1700       1710       1720       1730       1740
 CCCATTTGCA  GCAGCCCAAC  AAAGAAGGGC  AATTAGGTGT  TGGAATTGTG  GAAAGGAGGG
      1750        1760       1770       1780       1790       1800
 ACACTCGGCG  AAACAGTGCC  GAGCACCCAG  AAGACAGGGC  TGCTGGAAGT  GTGGCAAGTC
      1810        1820       1830       1840       1850       1860
 AGGACACATC  ATGGCAAACT  GCCCGGAAAG  ACAGGCAGGT  TTTTTAGGGA  TGGGCCCACG
      1870        1880       1890       1900       1910       1920
 GGGAAAGCAG  CCCCGCAACT  TCCCCGCGGC  CCAAGCTCCT  CAGGGGCTGA  TACCAACAGC
      1930        1940       1950       1960       1970       1980
 ACCCCCAATA  GATCCAGCAG  TGGACCTGTT  GGAGAAATAT  ATGCAGCAAG  GGAGAAAGCA
      1990        2000       2010       2020       2030       2040
 GAGAGAGCAG  AGGGAGAGAC  CATACAAGGA  GGTGACGGAG  GACTTACTGC  ACCTCGAGCA
      2050        2060       2070       2080       2090       2100
 GGGAGAGACG  CCCCACAGAG  GGGCGACAGA  GGACTTGCTA  CACCTCAATT  CTCTCTTTGG
      2110        2120       2130       2140       2150       2160
 AAAAGACCAG  TAGTCACAGC  ATTCATCGAG  GATCAGCCGG  TAGAAGTCTT  ACTAGACACA
      2170        2180       2190       2200       2210       2220
 GGAGCTGATG  ACTCAATAGT  AGCAGGAATA  GAGTTAGGGG  ACAATTACAC  TCCAAAAATA
      2230        2240       2250       2260       2270       2280
 GTGGGGGGAA  TAGGGGGATT  CATAAATACC  AAAGAATATA  AAAATGTAGA  AATAAAGGTA
      2290        2300       2310       2320       2330       2340
 CTAAATAAAA  GAGTAAGAGC  CACCATAATG  ACAGGAGATA  CCCCAATCAA  CATTTTTGGC
```

FIG. 4B

```
      2350       2360       2370       2380       2390       2400
 AGAAATATTC TGGCAACCTT AGGCATGTCA TTAAACCTAC CAGTCGCCAA GTTAGACCCA
      2410       2420       2430       2440       2450       2460
 ATAAAAGTAA CATTGAAGCC AGGGAAAGAT GGACCAAGGC TGAAACAATG GCCCCTAACA
      2470       2480       2490       2500       2510       2520
 AAAGAAAAAA TAGAAGCACT AAAAGAAATT TGTGAAAAAA TGGAAAGGGA GGGCCAACTA
      2530       2540       2550       2560       2570       2580
 GAAGAAGCAC CTCCAACTAA TCCTTATAAT ACCCCCACAT TTGCAATTAA GAAAAAGGAC
      2590       2600       2610       2620       2630       2640
 AAGAACAAAT GGAGAATGCT AATAGATTTT AGAGAACTAA ACAGGGTGAC TCAAGATTTC
      2650       2660       2670       2680       2690       2700
 ACAGAAATTC AGCTAGGAAT TCCACACCCG GCAGGATTAG CCAAAAAGAA AAGGATTACT
      2710       2720       2730       2740       2750       2760
 GTACTAGATG TAGGGGATGC CTACTTTTCC ATACCACTAC ATGAAGATTT TAGGCAATAT
      2770       2780       2790       2800       2810       2820
 ACTGCATTTA CCCTACCATC AGTAAACAAT GCAGAGCCAG AAAAAAGATA TGTATATAAG
      2830       2840       2850       2860       2870       2880
 GTCTTACCAC AAGGATGGAA AGGATCACCA GCAATCTTTC AATTCATGAT GAGGCAAATC
      2890       2900       2910       2920       2930       2940
 TTAGAACCTT TCAGAAAAGC AAACCCAGAC GTCATTCTCA TCCAATACAT GGATGATATC
      2950       2960       2970       2980       2990       3000
 TTAATAGCTA GTGACAGGAC GGGTTTAGAG CATGACAAAG TAGTCCTGCA ACTAAAAGAA
      3010       3020       3030       3040       3050       3060
 CTTCTGAATG GCCTAGGGTT CTCTACCCCA GATGAGAAGT TCCAAAAGGA CCCTCCGTTT
      3070       3080       3090       3100       3110       3120
 CAATGGATGG GCTATGAATT GTGGCCAACT AAATGGAAAC TGCAGAAAAT ACAATTACCT
      3130       3140       3150       3160       3170       3180
 CAGAAAGAAA TATGGACAGT CAATGACATC CAAAAACTAG TAGGAGTTTT GAACTGGGCG
      3190       3200       3210       3220       3230       3240
 GCGCAGATCT ATCCAGGGAT AAAAACCAAG CATTTATGTA AATTGATTAG AGGAAAAATG
      3250       3260       3270       3280       3290       3300
 ACACTCACAG AGGAAGTACA GTGGACAGAG TTAGCAGAGG CAGAACTAGA AGAAAACAAA
      3310       3320       3330       3340       3350       3360
 ATTATCTTAA GTCAGGAACA AGAGGGATCC TACTATCAGG AAGAAGAAGA ACTAGAAGCA
      3370       3380       3390       3400       3410       3420
 ACAGTCATCA AAAGCCAAGA CAATCAGTGG GCATACAAAA TACACCAGGG AGAGAGGGTT
      3430       3440       3450       3460       3470       3480
 CTAAAAGTAG GAAAGTATGC GAAGATAAAA AATACTCATA CCAATGGGGT CAGACTACTA
      3490       3500       3510       3520       3530       3540
 GCACAAGTAG TCCAAAAAAT AGGAAAGGAA GCACTGGTCA TTTGGGGACG AGTGCCAAAA
```

FIG. 4C

| 3550 | 3560 | 3570 | 3580 | 3590 | 3600 |
|---|---|---|---|---|---|
| TTTCACCTAC | CGGTAGAGAG | AGACACCTGG | GAGCAATGGT | GGGATAACTA | CTGGCAAGTA |
| 3610 | 3620 | 3630 | 3640 | 3650 | 3660 |
| ACATGGGTCC | CAGAGTGGGA | CTTCGTATCT | ACCCCACCAC | TGGTCAGGTT | GACATTTAAC |
| 3670 | 3680 | 3690 | 3700 | 3710 | 3720 |
| TTGGTAGGAG | ATCCTATACC | AGGCACAGAG | ACCTTTTACA | CAGATGGATC | ATGCAATAGA |
| 3730 | 3740 | 3750 | 3760 | 3770 | 3780 |
| CAGTCAAAAG | AAGGAAAAGC | AGGATATGTA | ACAGATAGAG | GGAGAGACAG | GGTAAGAGTA |
| 3790 | 3800 | 3810 | 3820 | 3830 | 3840 |
| TTAGAGCAAA | CATCCAATCA | GCAAGCAGAA | CTAGAAGCCT | TTGCGATGGC | ACTGGCAGAC |
| 3850 | 3860 | 3870 | 3880 | 3890 | 3900 |
| TCAGGTCCCA | AGGTTAATAT | CATAGTAGAC | TCACAGTATG | TAATGGGGAT | AGTAGCAGGC |
| 3910 | 3920 | 3930 | 3940 | 3950 | 3960 |
| CAACCAACAG | AGTCAGAAAA | TAGAATAGTA | AACCAAATCA | TTGAGGACAT | GATAAAGAAA |
| 3970 | 3980 | 3990 | 4000 | 4010 | 4020 |
| GAAGCAGTCT | ATGTTGCATG | GGTCCCAGCC | CATAAAGGCA | TAGGAGGAAA | CCAGGAAGTA |
| 4030 | 4040 | 4050 | 4060 | 4070 | 4080 |
| GACCATTTAG | TAAGTCAGGG | CATCAGACAA | GTATTATTCC | TGGAAAAGAT | AGAGCCCCGT |
| 4090 | 4100 | 4110 | 4120 | 4130 | 4140 |
| CAAGAAGAAC | ACGAAAATA | TCATAGCAAT | ATAAAGAAC | TAACCCATAA | ATTTGGAATA |
| 4150 | 4160 | 4170 | 4180 | 4190 | 4200 |
| CCCCAACTAG | TGGCAAGACA | GATAGTAAAC | ACATGTGCCC | AATGCCAACA | GAAAGGAGAA |
| 4210 | 4220 | 4230 | 4240 | 4250 | 4260 |
| GCCATACATG | GGCAAGTAAA | TGCAGAAATA | GGCGTTGGC | AAATGGACTG | CACACACTTA |
| 4270 | 4280 | 4290 | 4300 | 4310 | 4320 |
| GAAGGAAAAA | TCATTATAGT | AGCAGTGCAT | GTTGCAAGTG | GATTCATAGA | AGCAGAAGTC |
| 4330 | 4340 | 4350 | 4360 | 4370 | 4380 |
| ATCCCACAGG | AATCAGGAAG | GCAGACAGCA | CTCTTCCTAT | TAAAACTGGC | CAGTAGGTGG |
| 4390 | 4400 | 4410 | 4420 | 4430 | 4440 |
| CCAATAACAC | ACTTGCACAC | AGACAATGGC | CCCAACTTCA | CTTCACAGGA | AGTGAAGATG |
| 4450 | 4460 | 4470 | 4480 | 4490 | 4500 |
| GTGGCATGGT | GGATAGGTAT | AGAGCAATCC | TTTGGAGTAC | CTTACAATCC | ACAAAGCCAG |
| 4510 | 4520 | 4530 | 4540 | 4550 | 4560 |
| GGAGTAGTAG | AAGCAATGAA | TCACCACCTA | AAAAATCAGA | TAAGTAGAAT | TAGAGAACAG |
| 4570 | 4580 | 4590 | 4600 | 4610 | 4620 |
| GCAAATACAA | TAGAAACAAT | AGTACTAATG | GCAGTTCATT | GCATGAATTT | TAAAAGAAGG |
| 4630 | 4640 | 4650 | 4660 | 4670 | 4680 |
| GGAGGAATAG | GGGATATGAC | CCCAGCAGAA | AGACTAATTA | ACATGATCAC | CACAGAACAA |
| 4690 | 4700 | 4710 | 4720 | 4730 | 4740 |
| GAAATACAAT | TCCTCCAAAG | AAAAAATTCA | AATTTTAAAA | AATTCCAGGT | CTATTACAGA |

FIG. 4D

```
      4750       4760       4770       4780       4790       4800
  GAAGGCAGAG ATCAGCTGTG GAAAGGACCT GGAGAGCTAC TGTGGAAGGG AGACGGAGCA
      4810       4820       4830       4840       4850       4860
  GTCATAGTCA AGGTAGGGGC GGACATAAAA GTAGTACCAA GAAGGAAGGC CAAGATTATC
      4870       4880       4890       4900       4910       4920
  AGGGACTATG GAGGAAGGCA AGAACTGGAT AGTAGTTCCC ACCTGGAGGG TGCCAGGGAG
      4930       4940       4950       4960       4970       4980
  GATGGAGAGG TGGCATAGCC TTGTCAAGCA CCTGAAGTAC AGAACAAAAG ACTTAGAGGA
      4990       5000       5010       5020       5030       5040
  GGTGCGCTAT GTTCCCCATC ACAAGGTAGG ATGGGCATGG TGGACTTGCA GCAGGGTAAT
      5050       5060       5070       5080       5090       5100
  ATTCCCACTA GAAGGAGAAA GTCATCTAGA GATACAGGCA TATTGGAACC TAACACCAGA
      5110       5120       5130       5140       5150       5160
  AAAAGGATGG CTCTCCTCTC ATTCAGTAAG GTTAACCTGG TATACAGAAA AGTTCTGGAC
      5170       5180       5190       5200       5210       5220
  AGATGTTACC CCAGACTGTG CAGACTCCCT AATACACAGC ACTTATTTCT CTTGCTTTAC
      5230       5240       5250       5260       5270       5080
  GGCAGGTGAA GTAAGAAGAG CCATCAGAGG GGAAAAGTTA TTGTCCTGCT GCAACTACCC
      5290       5300       5310       5320       5330       5340
  CCAAGCTCAT AAAGCACAGG TACCATCACT TCAATACCTA GCCCTAGTGG TAGTGCAACA
      5350       5360       5370       5380       5390       5400
  AAATGGCAGA CCCCAGAGAA AGGGTGCCGC CAGGAAACAG TGGAGAAGAG ACCATTGGAG
      5410       5420       5430       5440       5450       5460
  AGGCCTTCGA GTGGCTAGAC AGGACTATAG AAGCCTTAAA ACGGGAGGCA GTGAACCATC
      5470       5480       5490       5500       5510       5520
  TGCCCCGAGA GCTCATTTTC CAGGTGTGGC AAAGGTCCTG GGCATATTGG CATGATGAAC
      5530       5540       5550       5560       5570       5580
  AAGGGATGTC AACAAGTTAC ACAAGTATA GATATTTGTG CATAATGCAG AAAGCTGTGT
      5590       5600       5610       5620       5630       5640
  ATATACATTT CAAGAAGGGG TGCACTTGCC TGGGAGAGG ACATGGCCCG GGAGGATGGA
      5650       5660       5670       5680       5690       5700
  GACCAGGACC TCCCCCTCCT CCCCCTCCAG GTCTAGTCTA ATGACTGAAG CACCAACAGA
      5710       5720       5730       5740       5750       5760
  GTTTCCCCCA GAAGATGGGA CCCCACGGAG AGAGCTAGGG AGTACCTGGG TAATAGAAAC
      5770       5780       5790       5800       5810       5820
  TCTGAAGGAA ATCAAGGAAG AAGCCTTAAA ACATTTTGAT CCCTGCTTGC TAATTGCTCT
      5830       5840       5850       5860       5870       5880
  TGGCAACTAT ATCTATAATA GACATGGAGA CACCCTTGAA GGAGCCAGAG AGCTCATTAG
      5890       5900       5910       5920       5930       5940
  AGTCCTACAA CGAGCCCTCT TCGTGCACAT CAGAGCGGGA TGTGACCGCT CAAGAAAGGG
```

FIG. 4E

```
      5950       5960       5970       5980       5990       6000
CCAAACAAGG AGAAGAGCTC CTTGCCCAGC TGCACCGACC CCTAGAGGCA TGCACTAACT
      6010       6020       6030       6040       6050       6060
CATGCTATTG TAAGCAGTGC AGTTACCATT GCCAGCTGTG TTTCTTGAAA AAAGGGCTCG
      6070       6080       6090       6100       6110       6120
GGATATGGTA TGCGCGACAG GGCAGACGAA GAAGGACTCC AAGAAAAACT AAGACTCATC
      6130       6140       6150       6160       6170       6180
CGCCTCCTGC ATCAGATAAG TAAGTATGGA GCCTGGTAGG AATCAGCTGC TTGTTGCCAT
      6190       6200       6210       6220       6230       6240
TTTATTAACT AGTGCTTGCT TAATATATTG CAAACAATAT GTGACTGTTT TCTATGGCAT
      6250       6260       6270       6280       6290       6300
ACCCGCGTGG AGAAATGCAT CTATTCCCCT ATTTTGTGCA ACCAAAAATA GAGATACTTG
      6310       6320       6330       6340       6350       6360
GGGGACCATC CAGTGCTTGC CAGACAATGA TGATTATCAG GAAATAACCT TAAATGTGAC
      6370       6380       6390       6400       6410       6420
AGAAGCTTTT GATGCATGGG ATAATACAGT AACAGAACAA GCAATAGAAG ATGTCTGGAG
      6430       6440       6450       6460       6470       6480
ACTGTTTGAG ACATCAATAA AACCATGTGT CAAGTTGACG CCCCTATGTG TGGCGATGAA
      6490       6500       6510       6520       6530       6540
TTGTAATATA ACTTCAGGGA CTACCGCGAC CCCGAGTCCA CCAAACATTA CAATAATAGA
      6550       6560       6570       6580       6590       6600
TGAAAATTCT ACCTGTATAG GCGACAACAA CTGCACAGGA TTAGGGAAAG AAGAGGTGGT
      6610       6620       6630       6640       6650       6660
TGAGTGTGAG TTCAATATGA CGGGGCTAGA ACAAGATAAG AAAAGGAAGT ATAATGACGC
      6670       6680       6690       6700       6710       6720
ATGGTACTCA AGAGATGTGG TTTGTGACAA GACAAACGGA ACAGGCACAT GTTACATGAG
      6730       6740       6750       6760       6770       6780
ACATTGCAAC ACATCAGTCA TCAAAGAGTC ATGTGACAAG CACTATTGGG ATGCTATGAA
      6790       6800       6810       6820       6830       6840
GTTAGATAC TGTGCACCAC CGGGTTTTGC CCTACTAAGA TGCAATGATA CCAACTATTC
      6850       6860       6870       6880       6890       6900
AGGCTTGAA CCTAAGTGCT CTAAAGTAGT AGCTGCTTCA TGCACAAGGA TGATGGAAAC
      6910       6920       6930       6940       6950       6960
GCAAACTTCT ACTTGGTTTG GCTTTAATGG CACTAGAGCA GOAOATAGAA CATATATCTA
      6970       6980       6990       7000       7010       7020
TTGGCATGGT AAOGATAATA GGACTATCAT TAGCTTAAAC AOGTATTATA ATCTCACAAT
      7030       7040       7050       7060       7070       7080
GCATTGTAAG AGACCAGGAA ATAAGACAGT TGTACCAATA ACACTTATGT CAGGGCGAAG
      7090       7100       7110       7120       7130       7140
GTTTCACTCT CGGCCAGTCT ACAACAAAAA ACCTGGGCAG GCATGGTGTT GGTTTCAAGG
```

FIG. 4F

```
      7150       7160       7170       7180       7190       7200
 CAACTGGATA GAAGCCATGC GGGAGGTGAA GCAAACCCTT GCAAAACATC CCAGGTACGG
      7210       7220       7230       7240       7250       7260
 AGGAACAAAT GATACAGGAA AAATTAACTT TACGAAGCCA GGAATAGGTT CAGACCCAGA
      7270       7280       7290       7300       7310       7320
 AGTGACATAC ATGTGGACTA ACTGCAGAGG AGAATTTCTC TACTGTAATA TGACTTGGTTT
      7330       7340       7350       7360       7370       7380
 CCTCAATTGG GTAGAAAATA AGACGAACCA AACACACGGC AACTATGCGC CATGCCATAT
      7390       7400       7410       7420       7430       7440
 AAGGCAGATA ATTAACACCT GGCATAAGGT AGGGACAAAT GTATATTTGC CTCCTAGGGA
      7450       7460       7470       7480       7490       7500
 AGGGGAGTTG ACCTGCAATT CAACAGTAAC CAGCATAATT GCTAACATTG ACTCAGATGG
      7510       7520       7530       7540       7550       7560
 AAATCAGACC AACATTACCT TTAGTGCAGA AGTGGCAGAA CTGTACCGAT TAGAATTGGG
      7570       7580       7590       7600       7610       7620
 GGACTACAAA TTGATAGAAG TAACACCAAT TCCGTTCGCA CCTACAAAAG AGAAAAGATA
      7630       7640       7650       7660       7670       7680
 TTCCTCGGCT CCAGTGAGGA ACAAAAGAGG TGTGTTCGTG CTAGGGTTCT TGGGTTTTCT
      7690       7700       7710       7720       7730       7740
 CGCAGCAGCA GGTTCTGCAA TGGGCGGCNC GTCCTTGACG CTGTCGGCTC AGTCCCGGAC
      7750       7760       7770       7780       7790       7800
 TTTACTGGCC GGGATAGTGC AGCAACAGCA ACAGCTGTTG GACGTGGTCA AGAGACAACA
      7810       7820       7830       7840       7850       7860
 AGAAATGTTG CGATTGACCG TCTGGGGAAC GAAAAATCTC CAGGCAAGAG TCACTGCTAT
      7870       7880       7890       7900       7910       7920
 CGAGAAATAC TTAAAGGACC AGGCACAGCT AAATTCATGG GGATGTGCGT TTAGGCAGGT
      7930       7940       7950       7960       7970       7980
 CTGCCACACT ACTGTACCAT GGGTAAATGA CTCCTTAACA CCTGACTGGA ACAATATGAC
      7990       8000       8010       8020       8030       8040
 ATGGCAGGAA TGGGAAAAAC GAGTCCACTA CCTAGAGGCA AATATCAGTC AAAGTTTAGA
      8050       8060       8070       8080       8090       8100
 ACAGGCACAA ATTCAACAAG AAAAGAATAT GTATGAACTA CAAAAACTAA ATAGCTGGGA
      8110       8120       8130       8140       8150       8160
 TGTCTTTGGC AACTGGTTTG ATTTGACCTC CTGGATCAAA TATATTCAAT ATGGAGTTTA
      8170       8180       8190       8200       8210       8220
 TATAGTAGTA GGAATAATAG GTTTAAGAAT AGCCATATAT ATAGTGCAAT TGTTAAGTAG
      8230       8240       8250       8260       8270       8280
 ACTTAGAAAG GGCTATAGGC CTGTTTTCTC CTCCCCCCCC GGTTATCTCC AACAGATCCA
      8290       8300       8310       8320       8330       8340
 TATCCACACG GACAGGGGAC AGCCAGCCAA CGAAGAAACA GAAGAAGACG CCGGAGACGA
```

FIG. 4G

```
     8350       8360       8370       8380       8390       8400
CAGTGGTTTC GGCTTGTGGC CTTGGCCACT AAACTACATA CAATTCCTGA TCCACCTACT
     8410       8420       8430       8440       8450       8460
GACTCGCCTC TTGACCGGGC TATACAACAG CTGCAGGGGC TTACTATCCA AGAACTCCCC
     8470       8480       8490       8500       8510       8520
GACCCGCCGA CTGATCTCCC AGAGTCTAAC AGCAATCAGG GACTGGCTGA GACTTAAGGC
     8530       8540       8550       8560       8570       8580
GGCCTACCTG CAATATGGGT GCGAGTGGAT CCAAGAAGCG TTCCGAGCAT TCGCAAGGAC
     8590       8600       8610       8620       8630       8640
TGCGAGAGAG ACTATTGCGG GCGCGTGGAG GGGGTTATGT GAAGCAGCGC AACGCATCGG
     8650       8660       8670       8680       8690       8700
GAGGGGAATC CTCGCAGTCC CAAGAAGGAT CAGGCAGGGA CCACAAATCC CCCTCCTCTC
     8710       8720       8730       8740       8750       8760
AGGGACAGCA GTATCAGCAG GGAGAGTTCA TGAACACCCC ATGGAGAACC CCAGCAGCAA
     8770       8780       8790       8800       8810       8820
TAGGGCAGAA AAATTCATAT AAGCAGCAAA ATATGGATGA TGTAGATTCT GATGATGATG
     8830       8840       8850       8860       8870       8880
ACCTAGTGGG AGTTCCTGTT ATGCCAAGAG TACCGCTGAG AGAAATGACC TATAAACTGG
     8890       8900       8910       8920       8930       8940
CAATAGATAT GTCACATTT ATAAAAGAAA AAGGAGGACT GGAAGGGATA TTTTACAGTA
     8950       8960       8970       8980       8990       9000
GGGAGAGACA TAGAATCCTA GACTTGTTCC TAGAAAAGGA GGAAGGGATA ATACCAGATT
     9010       9020       9030       9040       9050       9060
GGCAGAATTA TACTCATGGG CCAGGAACAA GGTACCCAAT GTACTTCGGG TGGCTGTGGA
     9070       9080       9090       9100       9110       9120
AACTAGTACC AGTAGACATC TCACAAGAGG CAGAGGAAGT AGAGACCAAC TGCTTAGTAC
     9130       9140       9150       9160       9170       9180
ACCCAGCACA AACAAGCAGA TATGATGACG AGCATGGGGA GACACTAGTT TGGCGGTTTG
     9190       9200       9210       9220       9230       9240
ACCCCATGCT GGCCTATAGT TACAAGGCCT TCATTCTGCA CCCAGAAGAA TTTGGGCACA
     9250       9260       9270       9280       9290       9300
AGTCAGGATT GCCAGAGAAA GAGTGGAAGG CAAAACTGAA AGCAAGAGGG ATACCATATA
     9310       9320       9330       9340       9350       9360
GTGAATAACA GGAACAACCA TACTTGGTCA GGGCAGGAAA TAGCTACTAA GAACAGCTGA
     9370       9380       9390       9400       9410       9420
GACTGCAGGG ACTTTCCAGA AGGGGCTGTA ACCAAGGGAG GGACATGGGA GGAGCTGGTG
     9430       9440       9450       9460       9470
GGGAACGCCC TCATATTCTC TGTATAAATG TACCCGCTTC TTGCATTGTA TTC
```

FIG. 5

HIV-D205; corresponding to position 8942-9255 in HIV-2 ROD; homology 71.6%

```
           10         20         30         40         50         60
    TGGAAGGGAT GTATTATAGT GAGAGAAGAC ACAGAATATT AGACACATAT TTTGAGAATG
           70         80         90        100        110        120
    AAGAAGGCAT TGTGTCTGGC TGGCAAAACT ATACTCATGG GCCAGGGATA AGGCATCCCA
          130        140        150        160        170        180
    AATACTTTGG TTGGCTGTGG AAGCTGGTAC CAGTAGAGGT GCCAGCAGCG ACCCGAGAGG
          190        200        210        220        230        240
    AGGAGGAAAC CCATTGCCTA ATGCACCCGG CACAGATCTC CTCATGGGAT GACATCCATG
          250        260        270        280        290        300
    GGGAGACTCT TATCTGGCAG TTTGATTCCC TCCTGGCATA TGATTATGTG GCTTTCAATA
          310
    GGTTTCCAGA  AGAGTTT
```

HIV-D205; corresponding to position 718-2510 in HIV-2 ROD; homology 78.6%

```
           10         20         30         40         50         60
    AAAAAATTCT TAAAGTCTTA GCTCCATTAG TACCAACAGG GTCAGAAAAT TTAAAAAGCC
           70         80         90        100        110        120
    TTTTTAATAT CGTCTGCGTC ATTTTTTGCC TGCACGCAGA AGAGAAAGTG AAAGATACAG
          130        140        150        160        170        180
    AGGAAGCAAA AAAGATAGCA CAGAGACATC TAGCGGCGGA CACAGAAAAA ATGCCAGCTA
          190        200        210        220        230        240
    CAAATAAACC AACAGCACCA CCTAGCGGCG GAAATTATCC AGTGCAGCAA CTGGCTGGCA
          250        260        270        280        290        300
    ACTACGTCCA CCTGCCGCTA AGCCCCCGAA CCTTAAATGC TTGGGTAAAG TTAGTAGAAG
          310        320        330        340        350        360
    AAAAGAAGTT CGGGGCAGAA GTAGTACCAG GATTTCAGGC ACTATCAGAA GGATGCACCC
          370        380        390        400        410        420
    CTTATGATAT AAATCAGATG CTAAATTGTG TAGGAGAACA TCAGGCAGCC ATGCAAATTA
          430        440        450        460        470        480
    TTAGAGAAAT AATCAATGAG GAAGCAGCAG ACTGGGACCA GCAACACCCG TCACCAGGCC
```

FIG. 5A

```
         490        500        510        520        530        540
    CAATGCCGGC AGGACAACTT AGGGACCCAA GAGGGTCAGA TATAGCAGGA ACCACCAGCA
         550        560        570        580        590        600
    CAGTAGAGGA ACAGATACAG TGGATGTACA GGGCCCAAAA TCCTGTCCCA GTGGGAAACA
         610        620        630        640        650        660
    TTTATAGAAG ATGGATTCAA TTAGGATTGC AGAAATGTGT CCGAATGTAC AATCCTACCA
         670        680        690        700        710        720
    ACATATTAGA CATAAAGCAG GGACCAAAGG AGCCCTTCCA AAGCTATGTA GATAGATTCT
         730        740        750        760        770        780
    ACAAAAGCTT ACGGGCAGAA CAAACAGACC CAGCAGTGAA AAATTGGATG ACACAAACAC
         790        800        810        820        830        840
    TGCTGATTCA GAATGCTAAC CCAGATTGCA AGTTAGTGCT TAAGGGCTTG GGAATGAATC
         850        860        870        880        890        900
    CCACCTTAGA GGAAATGCTA ACGGCCTGCC AAGGGATAGG AGGCCCAGGG CAGAAGGCAA
         910        920        930        940        950        960
    GGCTAATGGC CGAAGCCTTA AAAGAGGCCC TAACACCTGC ACCCATACCG TTTGCTGCCG
         970        980        990       1000       1010       1020
    TTCAACAAAA AGCAGGGAAG AGAGGGACAG TGACATGCTG GAACTGTGGC AAACAGGGAC
        1030       1040       1050       1060       1070       1080
    ACACAGCCAG GCAATGCAGG GCCCCTAGAA GACAGGGATG CTGGAAATGT GGAAAAACAG
        1090       1100       1110       1120       1130       1140
    GACACATCAT GTCAAAATGC CCAGAAAGAC AGGCGGGTTT TTTAGGGTTA GGACCCTGGG
        1150       1160       1170       1180       1190       1200
    GAAAGAAGCC TCGCAACTTC CCCATGACCC AAGTGCCTCA GGGAGTGACA CCATCTGCAC
        1210       1220       1230       1240       1250       1260
    CCCCGATGAA CCCAGCAGAG GGCATGACAC CTCGGGGGGC GACACCTCT GCGCCCCTG
        1270       1280       1290       1300       1310       1320
    CAGATCCAGC AGTGGAGATG CTGAAAAGTT ACATGCAGAT GGGGAGACAA CAGAGAGAGA
        1330       1340       1350       1360       1370       1380
    GCCGAGAGAG ACCCTACAAG GAGGTGACAG AGGATTTGCT GCACCTCAAT TCTCTCTTTG
        1390       1400       1410       1420       1430       1440
    GAGAAGACCA GTAGTCAAAG CATGTATCGA GGGTCAGTCA GTAGAAGTAT TACTAGACAC
        1450       1460       1470       1480       1490       1500
    AGGAGTTGAC GACTCAATAG TAGCAGGGAT AGAATTAGGT AGCAATTACA CCCCAAAAAT
        1510       1520       1530       1540       1550       1560
    AGTAGGAGGG ATAGGAGGGT TCATAAATAC CAAAGAATAC AAAGATGTAG AAATAGAAGT
        1570       1580       1590       1600       1610       1620
    AGTGGGAAAA AGAGTAAGGG CAACTATAAT GACAGGAGAT ACCCCAATAA ACATTTTTGG
```

FIG. 5B

| 1630 | 1640 | 1650 | 1660 | 1670 | 1680 |
|---|---|---|---|---|---|
| CAGAAATATT | TTAAATACCT | TGGGCATGAC | TTTAAATTTC | CCAGTGGCAA | AGGTAGAACC |
| 1690 | 1700 | 1710 | 1720 | 1730 | 1740 |
| AGTAAAAGTT | GAGTTAAAAC | CTGGAAAAGA | TGGGCCAAAG | ATCAGACAAT | GGCCTCTATC |
| 1750 | 1760 | 1770 | 1780 | 1790 | |
| CAGGGAAAAG | ATACTAGCCC | TCAAAGAAAT | CTGTGAAAAA | ATGGAAAAGG | |

HIV-D205; corresponding to position 2877-7293 in HIV-2 ROD; homology 75.1%

| 10 | 20 | 30 | 40 | 50 | 60 |
|---|---|---|---|---|---|
| AGGTATTAGA | TCCTTTTAGA | AAGGCCAACA | GCGATGTCAT | TATAATTCAG | TACATGGATG |
| 70 | 80 | 90 | 100 | 110 | 120 |
| ACATCCTTAT | AGCAAGTGAC | AGAAGTGATC | TGGAGCACGA | CAGGGTAGTG | TCCCAACTAA |
| 130 | 140 | 150 | 160 | 170 | 180 |
| AAGAGTTATT | AAATGACATG | GGATTCTCTA | CCCCAGAAGA | AAAGTTCCAA | AAAGACCCTC |
| 190 | 200 | 210 | 220 | 230 | 240 |
| CGTTCAAATG | GATGGGTTAT | GAGCTCTGGC | CAAAAAAGTG | GAAACTGCAA | AAAATACAAC |
| 250 | 260 | 270 | 280 | 290 | 300 |
| TGCCAGAAAA | AGAAGTTTGG | ACAGTGAATG | CAATTCAAAA | ACTGGTAGGA | GTATTAAACT |
| 310 | 320 | 330 | 340 | 350 | 360 |
| GGGCAGCTCA | ACTCTTTCCT | GGAATTAAGA | CAAGGCACAT | ATGCAAACTA | ATTAGGGGAA |
| 370 | 380 | 390 | 400 | 410 | 420 |
| AGATGACCCT | AACAGAAGAA | GTACAGTGGA | CAGAACTAGC | AGAAGCAGAG | CTACAGGAGA |
| 430 | 440 | 450 | 460 | 470 | 480 |
| ATAAAATCAT | CTTAGAACAG | GAACAAGAAG | GATCCTACTA | CAAGGAAAGG | GTACCGCTAG |
| 490 | 500 | 510 | 520 | 530 | 540 |
| AAGCAACAGT | ACAGAAAAAC | CTAGCAAATC | AGTGGACATA | CAAAATTCAT | CAGGGAAATA |
| 550 | 560 | 570 | 580 | 590 | 600 |
| AAGTCCTAAA | AGTAGGAAAA | TATGCAAAGG | TTAAAAACAC | GCACACCAAC | GGGGTAAGAC |
| 610 | 620 | 630 | 640 | 650 | 660 |
| TACTGGCACA | TGTAGTTCAG | AAAATAGGCA | AAGAAGCCCT | AGTCATCTGG | GGAGAGATAC |
| 670 | 680 | 690 | 700 | 710 | 720 |
| CAGTGTTCCA | TCTGCCAGTA | GAAAGAGAGA | CATGGGACCA | GTGGTGGACA | GATTACTGGC |
| 730 | 740 | 750 | 760 | 770 | 780 |
| AAGTAACCTG | GATCCCAGAG | TGGGACTTTG | TCTCGACCCC | ACCATTAATA | AGACTAGCCT |
| 790 | 800 | 810 | 820 | 830 | 840 |
| ACAACCTAGT | CAAAGACCCC | CTAGAAGGGA | GAGAAACCTA | CTACACAGAT | GGGTCCTGCA |

FIG. 5C

|      850 |      860 |      870 |      880 |      890 |      900 |
|----------|----------|----------|----------|----------|----------|
| ATAGAACCTC | AAAGGAAGGA | AAAGCAGGAT | ATGTCACTGA | CAGGGGAAAA | GATAAGGTTA |
|      910 |      920 |      930 |      940 |      950 |      960 |
| AAGTGTTAGA | ACAGACAACA | AACCAACAAG | CAGAACTTGA | AGCATTTGCA | TTAGCATTAA |
|      970 |      980 |      990 |     1000 |     1010 |     1020 |
| CAGACTCAGA | ACCACAAGTT | AACATCATAG | TAGATTCACA | ATATGTCATG | GGAATAATAG |
|     1030 |     1040 |     1050 |     1060 |     1070 |     1080 |
| CTGCACAGCC | AACAGAAACA | GAATCACCAA | TAGTAGCAAA | AATAATTGAA | GAAATGATCA |
|     1090 |     1100 |     1110 |     1120 |     1130 |     1140 |
| AAAAAGAGGC | AGTATATGTA | GGATGGGTAC | CAGCTCACAA | GGGACTGGGT | GGTAATCAGG |
|     1150 |     1160 |     1170 |     1180 |     1190 |     1200 |
| AAGTAGACCA | CCTAGTAAGT | CAAGGAATCA | GACAGGTCTT | GTTCCTAGAA | AAAATAGAAC |
|     1210 |     1220 |     1230 |     1240 |     1250 |     1260 |
| CAGCCCAGGA | AGAGCATGAA | AAATATCATG | GCAATGTAAA | AGAACTGGTC | CATAAATTCG |
|     1270 |     1280 |     1290 |     1300 |     1310 |     1320 |
| GAATTCCACA | ATTAGTGGCA | AAACAGATAG | TAAATTCCTG | TGATAAATGC | CAACAAAAAG |
|     1330 |     1340 |     1350 |     1360 |     1370 |     1380 |
| GGGAAGCTAT | TCATGGACAG | GTAAATGCAG | ACCTAGGGAC | ATGGCAGATG | GACTGTACAC |
|     1390 |     1400 |     1410 |     1420 |     1430 |     1440 |
| ATTTAGAAGG | AAAAATTATA | ATAGTGGCAG | TCCATGTAGC | CAGTGGGTTT | ATAGAAGCAG |
|     1450 |     1460 |     1470 |     1480 |     1490 |     1500 |
| AGGTAATACC | CCAAGAGACA | GGAAGACAGA | CAGCTCTCTT | CCTACTAAAG | TTGGCCAGCA |
|     1510 |     1520 |     1530 |     1540 |     1550 |     1560 |
| GATGGCCTAT | CACACACCTA | CACACAGACA | ACGGTGCCAA | CTTCACCTCA | CCAAGTGTAA |
|     1570 |     1580 |     1590 |     1600 |     1610 |     1620 |
| AGATGGTAGC | CTGGTGGGTA | GGAATAGAAC | AAACTTTTGG | AGTACCCTAT | AACCCACAAA |
|     1630 |     1640 |     1650 |     1660 |     1670 |     1680 |
| GTCAAGGAGT | AGTGGAAGCA | ATGAACCATC | ACCTGAAAAA | TCAAATAGAC | AGACTCAGAG |
|     1690 |     1700 |     1710 |     1720 |     1730 |     1740 |
| ACCAAGCAGT | ATCAATAGAG | ACAGTTGTAC | TAATGGCAAC | TCACTGCATG | AATTTTAAAA |
|     1750 |     1760 |     1770 |     1780 |     1790 |     1800 |
| GAAGGGGAGG | AATAGGGGAT | ATGACCCCTG | CAGAAAGACT | AGTTAACATG | ATAACCACAG |
|     1810 |     1820 |     1830 |     1840 |     1850 |     1860 |
| AGCAAGAAAT | ACAGTTCTTC | CAAGCAAAAA | ATTTAAAATT | TCAAAATTTC | CAGGTCTATT |
|     1870 |     1880 |     1890 |     1900 |     1910 |     1920 |
| ACAGAGAAGG | CAGAGATCAA | CTCTGGAAGG | GACCTGGTGA | ACTATTGTGG | AAAGGGGAAG |
|     1930 |     1940 |     1950 |     1960 |     1970 |     1980 |
| GAGCAGTCAT | CATAAAGGTA | GGGACAGAAA | TCAAAGTAGT | ACCCAGGAGA | AAAGCAAAAA |

FIG. 5D

| 1990 | 2000 | 2010 | 2020 | 2030 | 2040 |
|---|---|---|---|---|---|
| TTATAAGGCA | CTATGGAGGA | GGAAAAGGAT | TGGATTGTAG | TGCCGACATG | GAGGATACCA |
| 2050 | 2060 | 2070 | 2080 | 2090 | 2100 |
| GGCAGGCTAG | AGAGATGGCA | CAGTCTGATT | AAGTATCTTA | AGTATAGAAC | AGGAGAGTTG |
| 2110 | 2120 | 2130 | 2140 | 2150 | 2160 |
| CAACAGGTCT | CTTATGTCCC | TCACCACAAG | GTAGGATGGG | CTTGGTGGAC | TTGCAGTAGA |
| 2170 | 2180 | 2190 | 2200 | 2210 | 2220 |
| ATAATATTTC | CCCTAAACAA | AGGAGCATGG | CTAGAAGTCC | AAGGATATTG | GAACCTAACC |
| 2230 | 2240 | 2250 | 2260 | 2270 | 2280 |
| CCAGAAAGGG | GATTCTTGAG | CTCCTATGCT | GTAAGACTAA | CATGGTATGA | GAGGAACTTT |
| 2290 | 2300 | 2310 | 2320 | 2330 | 2340 |
| TATACAGATG | TAACACCTGA | TGTGGCAGAC | CAGCTACTGC | ATGGGTCTTA | TTTCTCTTGC |
| 2350 | 2360 | 2370 | 2380 | 2390 | 2400 |
| TTTTCAGCCA | ATGAAGTAAG | GAGAGCCATC | AGGGGAGAAA | AGATATTGTC | CTACTGCAAC |
| 2410 | 2420 | 2430 | 2440 | 2450 | 2460 |
| TATCCATCAG | CTCACGAAGG | GCAGGTACCA | AGCTTACAGT | TTCTAGCCCT | AAGGGTCGTA |
| 2470 | 2480 | 2490 | 2500 | 2510 | 2520 |
| CAGGAAGGAA | AAAATGGATC | CCAGGGAGAG | AGTGCCACCA | GGAAACAGCG | ACGAAGAAAC |
| 2530 | 2540 | 2550 | 2560 | 2570 | 2580 |
| AGTAGGAGAA | GCATTCGCTT | GGCTAGAAAG | AACAATAACA | GAGCTCAACA | GGGTAGCGGT |
| 2590 | 2600 | 2610 | 2620 | 2630 | 2640 |
| CAACCATTTG | CCCCGAGAAC | TTATTTTCCA | GGTCTGGCAG | AGGTCTTGGG | CATACTGGCG |
| 2650 | 2660 | 2670 | 2680 | 2690 | 2700 |
| TGAGGAACAG | GGCATGTCAA | TTAGCTATAC | CAAATATAGA | TACTTGTTGC | TAATGCAGAA |
| 2710 | 2720 | 2730 | 2740 | 2750 | 2760 |
| AGCAATGTTT | GTGCACTATA | CAAAGGGCTG | TAGGTGCCTG | CAGGAGGGCC | ATGGGCCAGG |
| 2770 | 2780 | 2790 | 2800 | 2810 | 2820 |
| GGGATNGAGA | TCAGGACCTC | CTCCTCCTCC | TCCCCCAGGC | CTGGCCTAAT | GGCAGAAGCA |
| 2830 | 2840 | 2850 | 2860 | 2870 | 2880 |
| GCCCCAGAGA | TCCCTCCAGA | GAACGAGAAC | CCACAAAGAG | AACCGTGGGA | AGAGTGGATA |
| 2890 | 2900 | 2910 | 2920 | 2930 | 2940 |
| GGGGAGATCC | TGGAGGAAAT | AAAGCAAGAA | GCCTTAAAGC | ATTTTGATCC | TCGCTTGCTA |
| 2950 | 2960 | 2970 | 2980 | 2990 | 3000 |
| ACTGCGCTTG | GTAACTTTAT | CTACAGTAGG | CATGGAGATA | CCCTTGCAGG | AGCAGGAGAG |
| 3010 | 3020 | 3030 | 3040 | 3050 | 3060 |
| CTCATTAAAA | TCCTCCAACG | AGCNCTCTTC | CTCCACTTCA | GAGCCGGTTG | TCAACACTCA |
| 3070 | 3080 | 3090 | 3100 | 3110 | 3120 |
| AGGATTGGAC | AATCAGGGGG | AGGAAATCCT | CTCTCAACTA | TACCGCCCCC | TTAAGGCATG |

FIG. 5E

```
    3130       3140       3150       3160       3170       3180
CGATAATACA TGCTACTGTA AGAAATGCTG CTACCATTGC CAGCTTTGTT TTCTTAAAAA
    3190       3200       3210       3220       3230       3240
GGGTCTTGGG ATATGTTATG ACCGCTCGAG AAGGAGATCT GCAAAAAGAG CTAAGACTAC
    3250       3260       3270       3280       3290       3300
TGCACCTTCT GCACCAGACA AGTGAGTATG GCATATTTTA GCAGCCGCCT GCCTATTGCG
    3310       3320       3330       3340       3350       3360
CTCCTGCTTA TAGGTATCAG TGGGTTTGTA TGTAAACAAT ATGTTACTGT CTTCTATGGC
    3370       3380       3390       3400       3410       3420
ATACCCGCAT GGAGGAACGC AACAGTTCCC CTCATTTGTG CAACCACAAA CAGAGACACC
    3430       3440       3450       3460       3470       3480
TGGGGAACTG TACAGTGTCT CCCAGACAAT GGTGACTACA CTGAGATCAG GCTAAACATA
    3490       3500       3510       3520       3530       3540
ACAGAGGCTT TTGATGCATG GGATAATACA GTGACACAAC AGGCAGTAGA TGATGTGTGG
    3550       3560       3570       3580       3590       3600
AGACTCTTTG AAACCTCCAT AAAACCATGT GTCAAACTAA CCCCACTGTG TGTGGCAATG
    3610       3620       3630       3640       3650       3660
AACTGTAGTA AAACCGAAAC AAACCCAGGG AATGCCAGTA GTACTACCAC CACTAAGCCT
    3670       3680       3690       3700       3710       3720
ACTACCACCT CTCGTGGGCT GAAAACGATT AACGAAACAG ACCCATGCAT AAAAAATGAC
    3730       3740       3750       3760       3770       3780
AGCTGCACAG GACTAGGAGA AGAGGAAATA ATGCAATGTA ATTTTAGTAT GACGGGACTA
    3790       3800       3810       3820       3830       3840
AGAAGAGATG AGCTAAAACA ATATAAAGAC ACCTGGTACT CAGAAGATTT AGAGTGTAAT
    3850       3860       3870       3880       3890       3900
AATACCAGGA AGTAATACCA GCAGTGCTAT ATAAGAACCT GCAACACAAC AATTATCCAA
    3910       3920       3930       3940       3950       3960
GAGTCATGTG ACAAACATTA TTGGGACAGC TTAAGGTTTA GGTATTGTGC TCCCCCGGGG
    3970       3980       3990       4000       4010       4020
TTTTTTCTAC TAAGATGTAA TGATACCAAC TATTCAGGCT TCATGCCCAA CTGCAGTAAG
    4030       4040       4050       4060       4070       4080
GTAGTAGCGT CCTCCTGCAC AAGAATGATG GAAACACAGT CCTCTACATG GTTTGGCTTC
    4090       4100       4110       4120       4130       4140
AATGGTACAA GGGCAGAGAA CAGGACATAT ATATATTGGC ATGAAAAAGA CAATAGGACC
    4150       4160       4170       4180       4190       4200
ATCATAAGCT TAAATACATA CTATAATTTG TCAATACACT GTAAGAGGCC AGGAAACAAG
    4210       4220       4230       4240       4250       4260
ACGGTTGTAC CAATAAGAAC CGTGTCAGGA CTACTTTTCC ATTCACAGCC TATCAATAAG
```

FIG. 5F

```
      4270        4280        4290        4300        4310        4320
AGACCCAGAC  AAGCTTGGTG  CTGGTTTAAG  GGAAACTGGA  CAGAAGCCAT  AAAGGAGGTG
      4330        4340        4350        4360        4370        4380
AAAAGGACCA  TCATAAAACA  TCCCAGGTAT  AAAGGAGGTG  CAAAAAATAT  CACAAGCGTA
      4390        4400        4410
AAGTTAGTAT  CAGAACATGG  AAAAGGTTCA  GATC
```

FIG. 6

|  | Position | nt ho | AA ho |
|---|---|---|---|
| R | 1-173 | 96.0 | |
| U5 | 174-299 | 94.4 | |
| 5'-untransl. | 300-545 | 93.5 | |
| gag | 546-2114 | 88.1 | 89.1 |
| pol | 1829-4939 | 88.7 | 89.6 |
| vif | 4869-5516 | 88.7 | 82.9 |
| vpx | 5344-5682 | 86.7 | 89.4 |
| vpr | 5682-5999 | 83.0 | 74.5 |
| tat ex 1 | 5845-6140 | 84.5 | 73.5 |
| rev ex 1 | 6071-6140 | 87.1 | 82.6 |
| tat ex 2 | 8307-8403 | 80.4 | 75.0 |
| rev ex 2 | 8307-8539 | 78.5 | 70.0 |
| nef | 8557-9327 | 82.6 | 73.9 |
| U3 | 8942-9496 | 85.4 | |

FIG. 7

| HIV-2D205,7 gene | position | HIV-2ROD | HIV-2NIHZ | HIV-2D194 | SIVMAC | SIVAGM | HIV-1BRU |
|---|---|---|---|---|---|---|---|
| gag | 720–1826 | 80.5/85.6 | | | | | |
| gag | 1860–2114 | 83.1/77.6 | | | | | |
| pol | 1859–2510 | 80.2/72.5 | | | | | |
| pol | 2877–4948 | 78.3/83.5 | | | | | |
| protease | 2084–2381 | 84.0/81.0 | 83.0/84.8 | 84.8/86.8 | 76.3/83.8 | 57.8/47.1 | 60.4/48.5 |
| vif | 4869–5516 | 72.0/68.5 | 70.9/67.9 | 72.4/66.5 | 71.8/60.6 | 53.8/34.7 | 47.9/33.0 |
| vpx | 5344–5682 | 76.1/74.1 | 73.5/68.1 | 74.6/77.9 | 75.2/77.0 | 50.8/34.7 | |
| vpr | 5682–5999 | 78.8/69.8 | 77.7/69.8 | 74.2/59.4 | 78.9/76.4 | | 51.9/47.3 |
| tatex1 | 5845–6140 | 78.4/66.3 | 79.1/68.4 | 74.7/63.3 | 81.1/66.3 | 33.1/38.1 | 33.6/34.0 |
| revex1 | 6071–6140 | 67.1/61.9 | 68.6/60.9 | 67.1/52.2 | 70.0/60.9 | 45.5/28.6 | 38.2/40.4 |
| nef | 8557–9255 | 72.1/69.5 | | | | | |
| env | 6147–7293 | 70.0/67.0 | | | | | |

FIG. 8

| HIV-2$_{D205,7}$ position | HIV-2$_{ROD}$ | HIV-2$_{NIHZ}$ | HIV-2$_{D194}$ | SIV$_{MAC}$ | SIV$_{AGM}$ | HIV-1$_{BRU}$ |
|---|---|---|---|---|---|---|
| 8942–9255 | 71.6 | 77.0 | 68.8 | 66.4 | 56.3 | 54.7 |
| 718–1825 | 80.5 | 80.8 | 80.3 | 79.1 | 65.1 | 63.8 |
| 1859–2510 | 80.2 | 74.6 | 75.0 | 78.8 | 55.6 | 56.9 |
| 2877–7293 | 75.1 | 74.8 | 75.4 | 74.0 | 58.0 | 54.6 |
| Total | 75.9 | 75.9 | 75.9 | 75.0 | 58.9 | 56.4 |

FIG. 10

|  | HIV-D194 (numbers refer to Fig. 4) | HIV-D205 (numbers refer to Fig. 5.1-5.3) | HIV-2 ROD (for comparison) (numbers refer to (Guyader et al.)) |
|---|---|---|---|
| gag | 547-2113 | 3-1394(5.2, part.) | 546-2114 |
| pol | 1831-4938 | 1049-1789 (5.2, part.) 3-2072 (5.3, part.) | 1829-4939 |
| vif | 4868-5515 | 1993-2643 (5.3) | 4869-5516 |
| vpx | 5343-5681 | 2474-2809 (5.3) | 5344-5682 |
| vpr | 5881-5998 | 2809-3126 (5.3) | 5682-5999 |
| tat exxon 1 tat exxon 2 | 5844-6139 8276-8372 | 2972-3261 (5.3) | 5845-6140 8307-8403 |
| rev exxon 1 rev exxon 2 | 6070-6140 8276-8517 | 3198-3261 (5.3, part.) | 6071-6140 8307-8539 |
| env | 6146-8701 | 3266-4413 (5.3, part.) | 6147-8720 |
| nef | 8535-9308 | 3-317 (5.1, part.) | 5557-9327 |

FIG. 11 gp 41/40

```
                          ProValArgAsnLysArgGly
5' -GGAATTCCATGGTACCAGTGAGGAACAAAAGAGGT
    CCTTAAGGTACCATGGTCACTCCTTGTTTTCTCCA.................
    EcoR1, Nco1, Kpn1
```

```
                Stop.....
..........TCGCCCTCCTGTGATAGTAAGCTTCC-3'
          AGCGGGAGGACACTATCATTCGAAGG
                                  Hind III
``` p24/27

```
                      ProValGlnGlnAla
5' -GGCCATGGTACCCGTGCAACAGGCAG
    CCGGTACCATGGGCACGTTGTCCGTC.................
    Nco1, Kpn1
```

```
             Stop.....
..........TGGAAAAGACCAGTAGTGATAAGCTTCC-3'
          ACCTTTTCTGGTCATCACTATTCGAAGG
                                  Hind III
```

HIV-2 VIRUS VARIANTS

This is a continuation of application Ser. No. 08/358,575, filed Dec. 14, 1994, now U.S. Pat. No. 5,637,455 which is a continuation of application Ser. No. 07/994,081, filed Dec. 16, 1992, now abandoned, which is a continuation of application Ser. No. 07/365,568, filed Jun. 14, 1989, now abandoned.

The present invention relates to HIV-2 virus variants, namely Virus HIV D194 and HIV D205 that may be cloned from the corresponding virus isolate HIV D194 (ECACC V 87122303) or from the infected cell line HUT 194 (ECACC V 87122306) and from the virus isolate HIV D205 (ECACC V 87122304), respectively, and to the RNA or RNA-fragments and derived therefrom DNA and DNA—fragments and/or proteins and the use thereof for diagnostics and therapy.

These variants are also described in "Molecular cloning of two West African human immunodeficiency virus type 2 isolates which replicate well on macrophages: a Gambian isolate from a case of neurologic acquired immunodeficiency syndrome, and a highly divergent Ghanesian isolate" (Kühnel, H., v. Briesen, H., Dietrich, U., Adamski, M., Mix, D., Biesert, L. Kreutz, R., Immelmann, A., Henco, K., Meichsner, Ch., Andreesen, R., Gelderblom, H. & Rübsamen-Waigmann, H., 1989, Proc. Natl. Acad. Sci. 86, 4, 2383–2387.

In diagnostics, two criteria are demanded to be met, namely specificity and sensitivity for the antigen to be detected. In the diagnostics of AIDS the demand for specificity can certainly be complied with by using the isolates HTLV-IIIB and LAV-2 (Guyader, M. et al., "Nature" 326, 1987, 662–669) in order to delimit HIV infections from other infections and, thus, to make a rough assignment into the classes of "HIV-2-related infections" or "HIV-1-related infections". However, a problem is constituted by the sensitivity of the diagnosis. In the range of the so-called seroconversion, i.e. the initial occurrence of the antibody in the infected person, a reduction in sensitivity implies an increase in the number of "falsely negative" test results. Accordingly, it is one main goal to shorten the period between an infection and the detectability of this infection as much as possible by improving the test sensitivity.

A decreased cross reactivity, in the practice of the widely employed ELISA diagnostics, is manifested, for example, in a reduced sensitivity. Thus, the use of the described HIV-1 isolate means about an average reduction of the test sensitivity against HIV-2 sera by the factor of 100 to 1000, whereas the isolate HTLV-IIIB enables almost no detection to be accomplished anymore.

A disastrous principle of the diseases caused by HIV resides in the fact that there is not only one type of each of HIV-1 and HIV-2 virus phenotypes and genotypes. What is to be premised is rather a large group of related viruses, possible even populations which by no way are strictly separated from each other but continuously penetrate one another and undergo some evolutionary development to a more and more increasing divergence, while at the same time they begin by recombination events to exchange between each other parts of the genome. Thus, the existing HIV species form a broad continuous population level in which there are no narrowly delimited subpopulations of one virus variant. There is rather to presumed that a continuum exists which is subject to permanent fluctuations with time.

The classified virus variants HIV-1 and HIV-2 are representatives of the diffusely delimited subpopulations having a relative low degree of relationship, which is manifested by only a partial cross reactivity. On the other hand, there are variants of the HIV-1 group (Rübsa-men-Waigmann, H. et al., "AIDS-Forschung" 10, 1987, 572–575; Rübsamen-Waigmann, H. et al., J. Med. Virol. 19, 1986, 335–344; v. Briesen, H. et al., J. Med. Vi-rol. 23, 1987, 51–66), which do significantly stronger cross-react with HIV-2 than the first characterized HIV-1 isolate itself (Hahn, B. et al., "Nature" 312, 1984, 166–169). A commercial product consisting of such an isolate diagnoses distinctly more sera as being HIV-2 positive than does the described standard isolate HTLV-IIIB.

An ideal diagnostic or therapeutic product should contain at least one representative from the populations as significantly biologically distinguished from one another.

HIV-1 viruses in a multitude of highly polymorphic genetic mutants may cause different diseases such as ARC, LAS, AIDS and encephalopathies (ARC: AIDS-related complex, LAS: lymphadenopathy syndrome, AIDS: acquired immune deficiency syndrome). Cloned virus variants are distinguished in sequence and restriction pattern, even if they have been isolated at the same time, at the same place and even from the same patient (Rübsamen, H. et al., 1986). It could be shown that virus variants of the HIV-1 type are distinguished in some virus antigens up to about 15%. HIV-2's are even different in more than 40% of the amino acids in some antigens, substitutions, insertions and deletions having been considered (Guyader, M. et al., 1987; Rabson, A. B. & Martin, M. A. "Cell" 40, 1985, 477–480).

The present invention provides two variants of the HIV-2 virus. One variant was isolated from a clinically asymptomatic patient, and one variant was isolated from a patient suffering from terminal so-called neuro-AIDS. The virus isolates proved to be diagnostic agents, relative to DNA/RNA as well as relative to the virus antigens, for serologically and directly identifying infections by the type HIV-2 in the pre-AIDS and AIDS stages.

The virus isolates according to the invention comprise viruses and proviruses, the characteristics of which are identical to those of the disclosed restriction map and the sequence of the cloned partial regions (FIGS. 2–8). Moreover, the virus isolates comprise variants which are distinguished from the viruses and proviruses described above in that they are different in their nucleotide sequences from the above-described viruses only by up to 5%, and preferably by 2%, particularly preferred by 1%.

The virus variants according to the invention may cause lymphadenopathies (further designated as LAS/AIDS) or serious neurological disorders (encephalopathies). Claimed according to the invention are also expression products of said virus variants, and more particularly antigens, preferably in accumulated or pure form, and processes for producing said expression products in full or in parts or in combinations of the parts. The expression products are intended to include all polypeptides in glycosylated and or meristylated forms which have been coded on the positive or negative strand of the cloned RNA or DNA.

A further preferred embodiment consists of cloned DNA sequences capable of hybridizing with genomic RNA and DNA of the virus variants. Claimed according to the invention are stable gen probes containing such DNA sequences which are suitable for the detection of hybridization of those and other HIV variants or related viruses or DNA proviruses in samples to be investigated, more particularly biological or semi-synthetic samples.

A further preferred embodiment of the invention is comprised by virus variants the RNA/DNA of which or respective fragments will hybridize to the virus variants according to the invention under stringent conditions, more particularly c-DNA, genomic DNA, recombinant DNA, synthetic DNA or fragments thereof. These are understood to include variants or fragments which exhibit deletions and insertions in comparison to the virus variants according to the invention.

Stringent conditions of hybridization and washing are meant to be understood as those conditions which ensue by way of experiment or calculation if the melting point of the 100% homologous nucleic acid complexes in conditions of hybridization and washing will be fallen below by not more than 5° C. under the buffer conditions employed.

Also claimed according to the invention are cloned synthetic gen probes which may be derived from the above-described virus variants and can be augmented in vector systems in eukaryotes or prokaryotes. The described cloned DNA fragments are suitable for hybridization with complementary nucleic acids (DNA/RNA) for the purpose of diagnostic detection of the virus variants. The diagnostic tests according to the invention are carried out by using DNA or RNA probes. The probes are radioactive or have been labelled with fluorescent bio- or chemiluminescent groups or enzymes or are specifically detectable with enzymes via coupled reaction systems. The hybridizations may be effected in a homogeneous phase of a solution or in a heterogeneous phase with solid-immobilized nucleic acids, while the solid may be a membrane, particle, cell or tissue, so that the hybridization may also be effected in situ.

From the virus isolates claimed according to the invention, the corresponding DNA sequences (FIG. 2) may be cloned in *E. coli* bacteria by establishing a genomic lambda-gen bank, starting from the DNA of the lymphocytes infected with the virus isolate. The desired clones are obtained by carrying out a plaque-screening with STLV-III sequences of the gag-pol range. In a more specific way, there may be used as a probe a DNA derived from the published sequence HIV-2 ROD (Guyader, M. et. al., "Nature" 326, 1987, 662–669), or a DNA probe derived from the partial sequences of the isolates HIV-2 D194 and HIV-2 D205 according to the invention. Thus from FIG. 3 a probe may be derived which under stringent conditions will hybridize only with variants of the type HIV-2 D194, however not with variants of the type HIV-2 ROD.

The diagnostic method based on the use of the viruses claimed according to the invention comprises the following steps: Extraction of RNA or DNA from biological samples, possibly enzymatic processing by restriction enzymes, separation by gel electrophoresis and/or direct blot methods for nucleic acid-binding carriers, and subsequent hybridization with parts of the cloned fragments of the claimed viruses. Hybridizations may also be directly carried out in chemically treated cells or tissues. Therein the origin of the tissues or liquids is insignificant.

Specifically, a process for the in vitro detection of antibodies against expression products of the viruses of the present invention is characterized in that the expression products or parts thereof of the viruses are detected by means of immunological methods. The process is characterized in that the expression products are proteins, peptides or parts thereof which have been coded within the meaning of an open reading frame on the DNA of the proviral partial sequences as characterized in FIG. 9 and are prepared by synthetic or biosynthetic processes.

The process is further characterized in that previously a definite amount or a combination of expression products or parts thereof are fixed on microtiter plates, whereupon subsequently biological samples, diluted or undiluted, are contacted with the coated microtiter plates and after incubation and sequential washing steps can be identified by means of a detecting reagent or of labelled anti-HIV antibodies.

Alternatively, filter strips and plastic strips or rods are used instead of microtiter plates, wherein the expression products of the viruses have been fixed at respective specific positions by isolated application of the different antigens.

The expression products or parts thereof can also be separated by gel electrophoresis and then transferred by blotting whereupon incubation with anti-HIV antibodies and the detection thereof are effected. Detection is effected on solid phase carriers to which the antigen determinants have been bonded, with the solid phase carrier consisting of particles.

Expression products can be virus antigens derived from in vitro-infected cells, said antigens being contacted with biological test materials as antigens bonded to fixed cells, and that the subsequent antibody bonding can be determined with immunological detection reagents by means of an apparatus, for example with a cytofluorimeter, or visually.

The antigens can be determined by competitive ELISA. HIV-related nucleic acids (DNA and RNA) can be detected in biological samples, cells and in isolated form by using the nucleic acids according to the present invention.

Expression products can be supplemented by materials which are related to other HIV variants, which, however, are distinguished in their biological properties from the materials of the isolates of the present invention.

For diagnostic and therapeutic goals the described DNA segments may also be employed for expressing coded antigens, parts thereof or combinations thereof with alien antigens. Therein the DNA segments under aimed control of regulation sequences are introduced into pro- or eukaryotic target cells, tissues or multiple-cell organisms to stimulate these to produce the accordingly coded antigens, parts thereof or combinations thereof with alien antigens. Antigens can be detected via the reaction with Anti-HIV-2 antibodies, more particularly from the sera of the respective patients. Antigens having longer open reading frames (>50 amino acids ) lend themselves as well those which are subject to splicing processes on the RNA level and are only thus composed to form the longer open reading frames.

According to the invention further claimed are polypeptides originating from the cloned virus variants according to the invention to detect such antigens in the material under investigation which contain similar antigen determinants and thereby do immunologically cross-react. This is particularly suitable for the diagnosis of AIDS and pre-AIDS of virus carriers or asymptomatic virus carriers or virus products, respectively, which are derived from blood. Also the serological detection of the antibodies directed against these antigenic polypeptides as expression products of the viruses claimed according to the invention becomes possible by employing conventional systems such as ELISA. The immunogenic polypeptides may be used as protective polypeptides as vaccines to cause protection against AIDS infections.

The polypeptides according to the invention are understood to include fragments which are intentionally obtained by means of gen-technological methods, starting from longer open reading frames as well as those obtained by proteolytic enzymes in the production bacterial strains or in vitro by the use of proteases.

The virus isolates according to the invention and the products derived therefrom may be combined with other isolates of the partial population HIV-2 in test systems, that is with those which are as far remote as possible in the described population level such as for example, the isolate HIV-2 ROD (Guyader, M. et al., 1987). Thereby it becomes possible sensitively to detect also populations of remote relationship in one test.

The virus variants according to the invention are highly different from the spectrum of the HIV-1 variants and have a closer molecular relationship to the HIV-2 virus described by Guyader, although they are distinguished therefrom to a significant extent (FIG. 1, FIG. 2, FIG. 3). Also the biological properties are clearly distinguished from the described HIV-2 isolate. Thus, the variants according to the invention, for the effective in vitro re-plication, prefer cells which are derived from myeloidic lines. On the contrary, the virus poorly reproduces itself on lymphocytic lines. This quality especially refers to HIV-D194.

The virus HIV D194 according to the invention exclusively caused encephalopathic symptoms in the infected patient, due to which the patient also deceased after an extremely short time and after a fulminant progress of the disease. Samples of the viruses claimed according to the invention have been deposited in the forms of their isolates at the European Collection of Animal Cell Cultures under the designations HIV D194 (Accession No. V 87122303) and HIV D205 (V 87122304), respectively, according to the Budapest Treaty.

A cell line infected with the virus isolate HIV D194 has been deposited under the designation HUT 194 (ECACC V 87122306) at the above-identified Deposit.

FIG. 1 shows the deviation of the proteins p24 and gp41 from lambda D194 and HIV-2 ROD 27/35 in its nucleotide sequence and amino acid sequence. (Guyader, M. et al., 1987, Nature 326, 662–669.)

FIG. 3 shows a comparative section of a sequence between HIV-2 ROD (Guyader, M. et al., 1987) and HIV-2 D194, which demonstrates the significant divergence of the variant HIV-2 D194 according to the invention in a coding range of the envelope protein gp120.

The section of the sequence shows a range of the gp120 region in comparison to the nucleotide sequence and the corresponding amino acid sequence in the single letter notation between HIV-2 D194 and HIV-2 ROD (Guyader, M. et al., 1987). The indication of the position refers to HIV-2 ROD. (–) symbolizes deletions/insertions. (.) symbolizes identical nucleotides.

FIGS. 4 and 4A–4G shows a nucleotide sequence, characterizing the clone HIV-D194. Nucleotide positions designated as N or O could not be unambiguously derived from the gel pattern. The sequence starts with R/U5 region the LTR and ends with U5 region.

The sequence shown is derived from subclone L10 (see restriction map). This clone differs from others derived from the same patient/blood sample by around 1% in the nucleotide sequence as it was determined by comparison with 5 kb homologous sequences derived from clone HIV-194.5.

Figure 2:
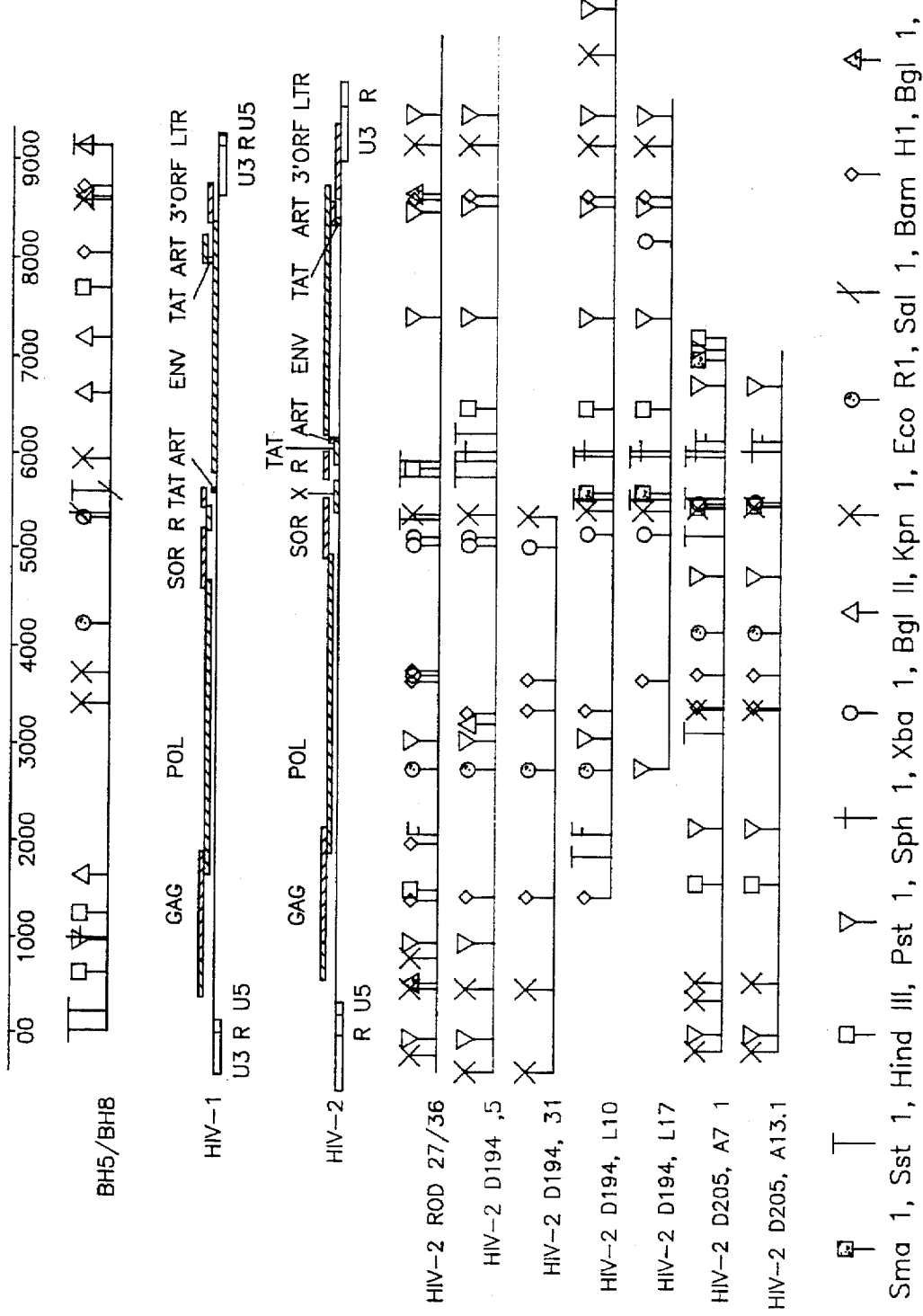
FIG. 2 shows the restriction maps of the virus isolates according to the invention in comparison to known HIV sequences.

FIGS. 5 and 5A–5F shows the partial nucleotide sequences of HIV-D205 (corresponding to clone HIV-2 A7.1 of FIG. 2).

FIG. 6 shows the sequence homology between HIV-D194 and HIV-2 ROD in (%), separately for the functional elements. The env region is not included because of the very much unrelated internal region shown in FIG. 3. (nt ho=nucleotide homology, AA ho=amino acid homology)

FIG. 7 shows the sequence homology of HIV-2 D205,7 compared to the HIV/SIV group (gene level; nt/aa).

FIG. 8 shows a nucleotide sequence comparison of HIV-2 D205 with HIV and SIV strains (in % homology).

Figure 9:
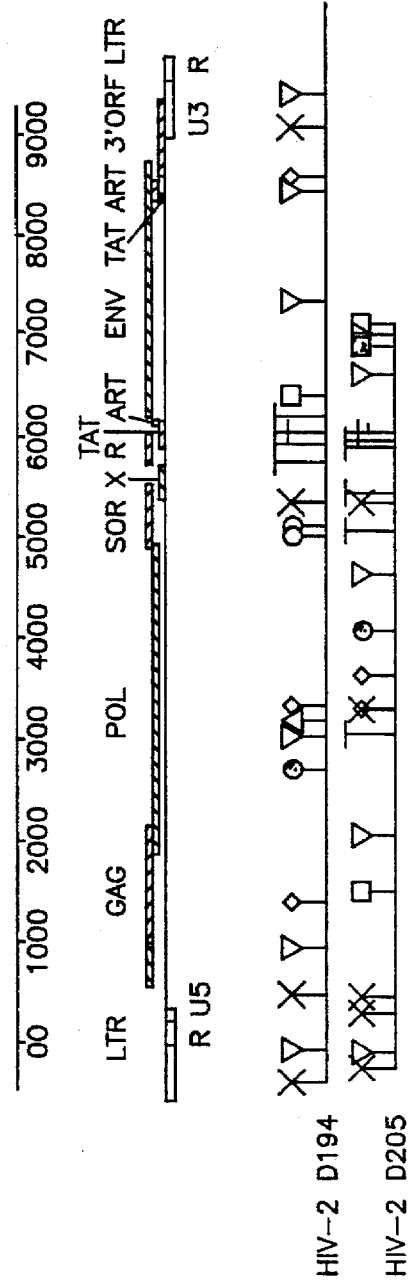

FIG. 9 shows the restriction maps of the proviral partial sequences of the isolates according to the invention.

FIG. 10 shows the correspondence of the open reading frames with functionally known antiviral antigens.

FIG. 11 shows the primer mediated constructions which are inserted as corresponding restriction fragments into the appropriate vectors.

Experimental results and characteristics of HIV-D194 and HIV-D205 are described in Kühnel, H. et al. (1989) Proc. Natl. Acad. Sci. 86, 4, 2383–2387.

The sequence of HIV-D194 shows a lot of so-called "open reading frames" as the fragments of HIV-D205 do. Most of these reading frames can be related to in vivo expressed proteins/antigens by comparison of homologies to previously described HIV-viruses, by comparison of Western blots performed with HIV-D194 and HIV-D205 antigens derived from infected HUT78 or U937 cells and by probing with sera from the corresponding patients and reference sera. FIG. 10 shows the correspondence of the open reading frames (numbers refer to FIGS. 4 and 5) with functionally known antiviral antigens.

Other open reading frames are not identified on the level of their expressed antigens defined by function or antibody staining on Western Blot. However, they can be expressed under some circumstances in vivo. Other leading frames, even short ones, can be expressed as well in a way difficult to predict solely on the basis of nucleic acid sequencing data because of splicing processes.

Antigenic determinants on expressed proteins as they are important for the biological function, for target antigens in diagnostics or for immunization are spread all over the expressed linear protein sequence. Parts of these sequences can have more general antigenic properties than others as can be shown by peptide screening/mapping for antigenic sites. These sites can be expressed as single epitopes or as continuous polypeptide or in a version of in vitro or synthetically spliced antigens. Antigenicity of the expressed products can be demonstrated by antigen fixation and blotting in the Western Blot assay. Constructions for antigen expression in E. coli can be done by using conventional techniques using synthetic genes, restriction fragments from cloned viral genome segments, trimming products thereof by using exonuclease or DNase I or by using sequence specific synthetic primers (FIG. 11) defining the desired 5' and 3' end of the fragment to be expressed together with appropriate restriction sites. These restriction sites can easily be used for ligation into a panel of expression vectors of different organisms like those derived from PLc24 (Remault et al. 1981 Gene 15, 81–83) with multicloning sites (pEX).

The expressed antigens were shown to specifically react with patients' sera. The p27(24) from gag of HIV-D205 react very sensitively with both typical HIV-1 sera and typical HIV-2 sera (see Kühnel et al). The antigenic sequence corresponding to the region shown in FIG. 3 is highly specific for this particular subfamily of HIV-variants.

EXAMPLE 1

Cloned subfragments such as the Kpn-Kpn fragment comprising the gag-pol region of HIV-D194 are used as probes for HIV-2 type and SIV type sequences by hybridizing under conditions 30°–40° C. less in hybridization and washing conditions appropriate for homologous sequences.

The hybridization of homogenous DNA double helices is usually performed at temperatures of 20°–25° C. below Tm. Tm as the corresponding melting temperature is calculated in an approximation as Tm=81.5° C.+16.6 log M+0.41 (% G+C)−500/n×0.61 (% formamide ) (see J. Meinkoth & G. Wahl, Anal. Biochem. 138 (1984) 267–284; Boiton, E. T. & McCarthy, B. J., Proc. Natl. Acad. Sci., U.S.A. 488 (1962 ) 1390–1397 ). Stringent washing conditions for homogenous DNA-double helices are chosen around 5° C. below the Tm calculated as above.

HIV-1 sequences do not show up in blot and in situ hybridization unambiguously, although this region contains the p24/27 coding region which heavily cross-reacts with anti HIV-1 sera. A nucleic acid probe such as shown in and corresponding to FIG. 3, however, highly specifically detects the specific subfamily of HIV-D194 compared to all other known HIV isolates. This is shown by in situ hybridization using run-off RNA of this particular region.

We claim:

1. A cell transfected with a viral agent wherein the viral agent is virus isolate HIV D194 (ECACC V 87122303) or virus isolate HIV D205 (ECACC V 87122304).

2. A process for producing a protein comprising culturing the transfected cell of claim 1 and recovering viral protein expressed by the viral agent.

3. Cell line HUT 194 (ECACC V 87122306).

4. A process for producing protein comprising culturing cells from the cell line of claim 3, and recovering viral protein expressed, thereby.

* * * * *